United States Patent [19]
Heins et al.

[11] Patent Number: 6,060,051
[45] Date of Patent: May 9, 2000

[54] STRAIN OF BACILLUS FOR CONTROLLING PLANT DISEASES AND CORN ROOTWORM

[75] Inventors: Sherry Darlene Heins; Denise Carol Manker, both of Davis; Desmond Rito Jimenéz, Woodland; Randy Jay McCoy, Davis; Pamela Gail Marrone, Davis; Jimmy Ensio Orjala, Davis, all of Calif.

[73] Assignee: AgraQuest, Inc., Davis, Calif.

[21] Appl. No.: 09/074,870

[22] Filed: May 8, 1998

Related U.S. Application Data

[63] Continuation-in-part of application No. 08/853,753, May 9, 1997.

[51] Int. Cl.$^7$ ............................ A01N 63/00; A01N 25/00; A61K 35/00; C12N 1/20
[52] U.S. Cl. ................................. 424/93.462; 424/93.46; 424/115; 424/123; 424/404; 424/405; 435/71.1; 435/71.2; 435/71.3; 435/252.5; 435/839
[58] Field of Search ............................ 424/93.46, 93.462, 424/404, 405, 115, 123; 435/71.1, 71.2, 71.3, 252.5, 839

[56] References Cited

U.S. PATENT DOCUMENTS

| | | |
|---|---|---|
| 4,904,585 | 2/1990 | Shimada et al. . |
| 4,999,192 | 3/1991 | Payne et al. . |
| 5,045,314 | 9/1991 | Bone et al. ............................ 424/93.46 |
| 5,047,239 | 9/1991 | Pusey . |
| 5,049,379 | 9/1991 | Handelsman et al. . |
| 5,055,293 | 10/1991 | Aronson et al. ...................... 424/93.46 |
| 5,061,495 | 10/1991 | Rossall . |
| 5,187,091 | 2/1993 | Donovan et al. . |
| 5,208,017 | 5/1993 | Bradfisch et al. . |
| 5,344,647 | 9/1994 | Rossall . |
| 5,403,583 | 4/1995 | Liu et al. . |
| 5,597,565 | 1/1997 | Leifert et al. . |
| 5,645,831 | 7/1997 | Chilcott et al. ..................... 424/93.461 |
| 5,733,544 | 3/1998 | Marrone et al. ...................... 424/93.46 |
| 5,753,222 | 5/1998 | Marrone et al. .................... 424/93.462 |

FOREIGN PATENT DOCUMENTS

| | | |
|---|---|---|
| 61-051504 | 9/1987 | Japan . |
| WO 96/10083 | 4/1996 | WIPO . |

OTHER PUBLICATIONS

Kimura et al., "SNA–60–367, new peptide enzyme inhibitors against aromatase" *J. Antibiot.* 50(6):529–531 (1997).
Tsuge et al., "Characterization of *Bacillus subtilis* YB8, coproducer of lipopeptides surfactin and plipastatin B1" *J. Gen. Appl. Microbiol.* 41(6):541–545 (1995).
Argauer et al., "Evidence for a novel insecticidally active exotoxin produced by the HD 116 strain of *Bacillus thuringiensis* var. morrison" *J. Entomol Sci.* 26(2):205–213 (1991).
Arima et al., "Surfactin, A crystalline peptidelipid surfactant produced by *Bacillus subtilis*: Isolation, charcaterization and its inhibition of fibrin clot formation" *Biochem. Biophys. Res. Commun.* 31(3):488–494 (1968).

Asaka, O. and Shoda, M., "Biocontrol of *Rhizoctonia solani* damping–off of tomato with *Bacillus subtilis* RB14" *Appl. Environ. Microbiol.* 62(11):4081–4085 (1996).
Baker et al., "Inhibitory effect of *Bacillus subtilis* on *Uromyces phaseoli* and on development of rust pustules on bean leaves" *Phytopathology* 73:1148–1152 (1983).
Besson et al., "Antifungal activity upon *Saccharomyces cerevisiae* of iturin A, mycosubtilin, bacillomycin L and of their derivatives: Inhibition of this antifungal activity by lipid antagonists" *J. Antiobiotics* 32(8):828–833 (1979).
Bland et al., "Iturin–A antifungal peptide produced by *Bacillus subtilis*" *Proc. Plant Growth Regulation Soc. Am.* 22nd:102–107 (1995).
Bochner, "Sleuthing out bacterial identities" *Nature* 339:157–158 (1989).
Burgerjon et al., "Alimentation au laboratoire de *Perillus bioculatus* Fabr. avec des larves de *Leptinotarsa decemlineata* Say intoxiquées par la toxine thermostable de *Bacillus thruingiensis* Berliner" *Entomophaga* 11; 279–284 (1979). An English summary is contained on p. 283.
Cleveland, Jr., "Using cotton marketing alternatives" *Proc. 1987 Beltwide Cotton Prod. Conf.*, J.M. Brown, Conf. Coordinator, Dallas, TX, pp. 43–44 (Jan. 4–8, 1987).

(List continued on next page.)

*Primary Examiner*—Leon B. Lankford, Jr.
*Assistant Examiner*—Christopher R. Tate
*Attorney, Agent, or Firm*—Antoinette F. Konski; Baker & McKenzie

[57] ABSTRACT

The present invention relates to a novel antibiotic-producing and metabolite-producing *Bacillus subtilis* strain that exhibits insecticidal, antifungal and antibacterial activity. The supernatant of this novel strain contains effective insecticidal, antifungal and antibacterial agents. Also included in the invention is a solvent extractable, small molecular weight (<10,000 daltons) corn rootworm-active metabolite produced in the supernatant. Also included in the invention are methods of protecting or treating plants from fungal and bacterial infections and corn rootworm infestations comprising the step of applying to the plant an effective amount of the antibiotic/metabolite-producing novel *Bacillus subtilis* strain, the antibiotic/metabolite produced by the novel *Bacillus subtilis* strain or a combination thereof, optionally further comprising another antibiotic-producing bacterial strain and/or a chemical pesticide. The invention also includes methods of preventing or treating fungal and bacterial infections using whole broth cultures or supernatants obtained from cultures of the novel *Bacillus subtilis* strain alone or in combination with chemical pesticides and/or other biocontrol agents. The invention also includes novel antifungal and antibacterial compounds designated agrastatins and a novel combination comprising an A-type iturin, a plipastatin, a surfactin and an agrastatin. Methods of treating or protecting plants from fungal and bacterial infections and corn rootworm infestations comprising administering the novel agrastatins and the novel combination comprising an A-type iturin, a plipastatin, a surfactin and an agrastatin are provided.

24 Claims, 2 Drawing Sheets

OTHER PUBLICATIONS

Estruch et al., "Transgenic plants: An emerging approach to pest control" *Nature Biotechnology* 15:137–141 (1997).

Ethridge, "Market pricing based on fiber properties" *Proc. 1987 Beltwide Cotton Prod. Conf.*, J. M. Brown, Conf. Coordinator, Dallas, TX, pp. 44–46 (Jan. 4–8, 1987).

Ferreira et al., "Biological control of *Eutypa lata* on grapevine by an antagonistic strain of *Bucillus subtilis*" *Phytopathology* 81:283–287 (1991).

He et al., "Zwittermicin A, an antifungal and plant protection agent from *Bacillus cereus*" *Tetrahedron Lett.* 36(16):2499–2502 (1994).

Hiraoka et al., "Characterization of *Bacillus subtilis* RB14, coproducer of peptide antibiotics iturin A and surfactin" *J. Gen. Appl. Microbiol.* 38:636–640 (1992).

Huang et al., "Nucleotide sequence and characteristics of the gene, Ipa–14, responsible for biosynthesis of the lipopeptide antibiotics iturin A and surfactin from *Bacillus subtilis* RB14") *J. Ferment. Bioeng.* 76(6):445–450 (1993).

Islam, K.Z. and Nandi, B., "Control of brown spot of rice by *bacillus megaterium*" *J. Plant Disease and Protection* 92(3):241–246 (1985).

Islam, et al., "Inhibition of some fungal pathogens of host phylloplane by *Bacillus megaterium*" *J. Plant Disease Protection* 92(3):233–240 (1985).

Johnson et al., "Insecticidal activity of EG4961, a novel strain of *Bacillus thuringiensis* toxic to larvae and adults of Southern corn rootworm (Coleoptera: Chrysomelidae) and Colorado potato beetle (Coleopetra: Chrysomelidae)" *J. Econ. Entomol.* 86:330–333 (1993).

Kakinuma et al., "Determination of fatty acid in surfactiv and elucidation of the total structure of surfactin" *Agric. Biol. Chem.* 33(6):973–976 (1969).

Latoud et al., "Interactions of antiobiotics of the iturin group with human erythrocytes" *Biochim. Biophys. Acta* 856:526–535 (1986).

Leifert et al., "Antibiotic production and biocontrol activity by *Bacillus subtilis* CL27 and *Bacillus pumilus* CL45" *J. Appl. Bacteriol.* 78:97–108 (1995).

Lúthy, "Insecticidal toxins of *Bacillus thuringiensis*" *FEMS Microbiol Lett.* 8:1–7 (1980).

Marrone et al., "Improvements in laboratory rearing of the Southern Corn rootworm, *Diabrotica undecimpuncta howardi barber* (Coleptera: Chrysomelidae), on an artifical diet and corn" *J. Econ. Entomol.* 78:290–293 (1985).

McKeen et al., "Production and partial characterization of antifungal substances antagonistic to *Monilinia fructicola* from *Bacillus subtilis*" *Phytopathology* 76(2):136–139 (1986).

Milner et al., "Production of kanosamine by *Bacillus cereus* UW85" *Appl. Environ. Microb.* 62(8):3061–3065 (1996).

Nishikiori et al., "Plipastatisn: New Inhibitors of phospholipase $A^2$ produced by *Bacillus cereus* BMG302–fF67" *J. Antibiotics* 39(6):755–761 (1986).

Ohno et al., "Production of antifungal antibiotic, iturin in a solid state fermentation by *Bacillus subtilis* NB22 using wheat bran as a substrate" *Biotech Lett.* 14(9):817–822 (1992).

Ohno et al., "Effect of temperature change and aeration on the production of the antifungal peptide antibiotic iturin by *Bacillus subtilis* NB22 in liquid cultivation" *J. Ferment. Bioeng.* 75(6):463–465 (1993).

Ohno et al., "Effect of temperature on production of lipopeptide antibiotics, iturin A and surfactin by a dual producer, *Bacillus subtilis* RB14, in solid–state fermentation" *J. Ferment. Bioeng.* 80(5):517–519 (1995).

Osburn et al., "Effect of *Bacillus cereus* UW85 on the yield of soybean at two field sites in Wisconsin" *Am. Phytopathol. Soc.* 79(6):551–556 (1995).

Parvin et al., "Cost effectiveness of harvesting at the right time" *Proc. 1987 Beltwide Cotton Prod. Conf.*, J.M. Brown, Conf. Coordinator, Dallas, TX, pp. 39–42 (Jan. 4–8, 1987).

Parvin et al., "The economics of cotton harvesting in the midsouth as it relates to shorter season production systems" *Proc. 1987 Beltwide Cotton Prod. Conf.*, J.M. Brown, Conf. Coordinator, Dallas, TX, pp. 79–81 (Jan. 4–8, 1987).

Peypoux et al., "Structure de l'iturine C de *Bacillus subtilis*" *Tetrahedron* 34(8):1147–1152 (1978).

Phae, C–G. and Shoda, M., "Investigation of optimal conditions for foam separation of iturin, an antifungal peptide produced by *Bacillus subtilis*" *J. Ferment. Bioeng.* 71(2):118–121 (1991).

Pusey et al., "Pilot tests for commercial production and application of *Bacillus subtilis* (B–3) for postharvest control of peach brown rot" *Plant Dis.* 72(7):622–626 (1988).

Sandrin et al., "Coproduction of surfactin and iturin A, lipopeptides with surfactant and antifungal properties, by *Bacillus subtilis*" *Biotechnol. Appl. Biochem.* 12:370–375 (1990).

Schwinn et al., "Control with chemicals" *Advances in Plant Pathology: Vol. 7, Phytophtohora infestans,* The Cause of Late Blight of Potato, Academic Press, San Diego Chapter 8, pp. 225–265 (1991).

Sholberg et al., "Biocontrol of postharvest disease of apple using *Bacillus spp.* isolated from stored apples" *Can. J. Microbiol.* 41:247–252 (1995).

Singh et al., "*Bacillus subtilis* as a control agent against fungal pathogens of citrus fruit" *Trans. Br. Mycol. Soc.* 83(3):487–490 (1984).

Smith et al., "Suppression of cottony leak of cucumber with *Bacillus cereus* strain UW 85" *Plant Dis.* 77(2):139–142 (1993).

Stabb et al., "Zwittermicin A–producing strains of *Bacillus cereus* from diverse soils" *Applied Environ. Microbiol.* 60:4404–4412 (1994).

Stonard et al., "Microbial secondary metabolites as a source of agrochemicals" *ACS Symposium Series,* Chapter 3, pp. 25–36 (1994).

Swinburne et al., "Production of antibiotics by *Bacillus subtilis* and their effect on fungal colonists of apple leaf scars" *Trans. Brit. Mycol. Soc.* 65(2):211–217 (1975).

Umezawa et al., "Plipastatins: New Inhibitors of phospholipase $A_2$,produced by *Bacillus cereus* BMG302–fF67" *J. Antibiotics* 39(6):737–744 (1986).

Yamada et al., "Biological activity of antifungal substances produced by *Bacillus subtilis*" *J. Pesticide Sci.* 15(1):95–96 (1990).

STRAIN OF BACILLUS FOR CONTROLLING PLANT DISEASES AND CORN ROOTWORM

CROSS REFERENCE TO RELATED APPLICATIONS

This application is a continuation-in-part of Ser. No. 08/853,753, filed May 9, 1997.

FIELD OF THE INVENTION

The present invention is in the field of biopesticides. More particularly, this invention relates to the finding that a novel strain of *Bacillus subtilis*, AQ713, can inhibit a broad range of fungal and bacterial plant diseases and also have activity against corn rootworm. The invention also relates to fungicidal, bactericidal, and insecticidal compositions comprising this novel Bacillus strain and the antibiotics and metabolites produced by this strain either alone, or in combination with other chemical and biological pesticides.

BACKGROUND OF THE INVENTION

For a number of years, it has been known that various microorganisms exhibit biological activity so as to be useful to control plant diseases. Although progress has been made in the field of identifying and developing biological pesticides for controlling various plant diseases of agronomic and horticultural importance, most of the pesticides in use are still synthetic compounds. Many of these chemical fungicides are classified as carcinogens by the EPA, are toxic to wildlife and other non-target species. In addition, pathogens may develop resistance to chemical pesticides (see, e.g., Schwinn et al., p. 244, ADVANCES IN PLANT PATHOLOGY: *PHYTOPHTHORA INFESTANS*, THE CAUSE OF LATE BLIGHT OF POTATO (Academic Press, San Diego 1991).

Every year 250–300 million dollars of chemical pesticides are used to control corn rootworm infestations. Many of these chemical pesticides are toxic to humans, wildlife and other nontarget species. Also some have been found in the ground water. New chemical insecticides cost $100 million to develop.

Biological control offers an attractive alternative to synthetic chemical fungicides. Biopesticides (living organisms and the naturally produced compounds produced by these organisms) can be safer, more biodegradable, and less expensive to develop.

Screening programs have identified certain Bacillus spp. (Bacillus spp. includes *B. subtilis, B. cereus, B. mycoides, B. thuringiensis*) strains that exhibit antifungal activity. (See e.g. Stabb et al. (1990) *Applied Environ. Microbiol.* 60: 4404–4412). These strains have been shown to produce zwittermicin-A and or kanosamine (Milner et al. (1996) *Appl. Environ. Microb.* 62: 3061–3066), two antibiotic agents that are effective against the soil borne disease damping off, caused by *Phytophthora medicaginis, P. nicotianae, P. aphanidermatum* or *Sclerotinia minor* (See Stabb et al., supra). Zwittermicin-A is a water soluble, acid stable linear aminopolyol molecule (see, He et al, (1994) Tetra. Lett. 35 (16) 2499–2502.

U.S. Pat. No. 5,049,379 to Handelsman et al. describes how zwittermicin-A produces damping off in alfalfa and soybeans. When the seed was coated with *B. cereus* ATCC 53522, the pathogenic activity of root rot fungus is inhibited. Similarly application of spore-based formulations of certain *B. cereus* strains to soybean seeds or the soil surrounding the seeds has been shown to improve soybean yield at field sites. (See, Osburne et al (1995) *Am. Phytopathol. Soc.* 79(6): 551–556). Methods of applying biopesticides are well known in the art and include, for example, wettable powders, dry flowables, microencapsulation of effective agents, liquid or solid formulations of antibiotic fractions from suitable cultures. (See e.g., U.S. Pat. No. 5,061,495 to Rossall or U.S. Pat. No. 5,049,379 to Handelsman).

Smith et al. (1993) *Plant Disease* 77(2) 139–142 report that the activity of the soil-borne fungus, *Pythium aphanidermatum,* that causes cottony cucumber leak can be suppressed using zwittermicin-producing *B. cereus* strain UW85. Leifert et al. (1995) *J. Appl. Bacteriol.* 78: 97–108 report that the production of anti-Botrytis and anti-Alternaria antibiotics by two Bacillus strains, *B. subtilis* CL27 and *B. pumilis* CL 45. The whole broth and cell-free filtrates were active against Botrytis and Alternaria in in vitro tests and were active against Botrytis in in vivo small plant tests on Astilbe. Leifert et al. (1997) U.S. Pat. No. 5,597,565 disclose *B. subtilis, B. pumilis, and B. polymyxa* that are particularly effective at inhibiting post harvest disease causing fungi. They also disclose the presence of antibiotics produced in the cell-free culture filtrate and their activity at different pH values, but they do not identify these compounds.

Rossall (1994) U.S. Pat. No. 5,344,647 discloses *Bacillus subtilis* strains with broad anti-fungal activity. Sholberg et al. (1995) *Can. J. Microbiol.* 41: 247–252, Swinburne et al. (1975) *Trans. Brit. Mycol. Soc.* 65: 211–217, Singh and Deverall (1984) *Trans. Br. Mycol. Soc.* 83: 487–490, and Ferreira, et al. (1991) *Phytopathology* 81: 283–287. Baker et al. (1983) *Phytopathology* 73: 1148–1152 disclose the use of Bacillus spp. and *Bacillus subtilis* as biocontrol agents of fungal plant pathogens. Baker et al. (1983) *Phytopathology* 73: 1148–1152 also report on an antifungal *Bacillus subtilis* for use on plant pathogens. Pusey et al. (1988) *Plant Dis.* 72: 622–626, Pusey and Robins (U.S. Pat. No. 5,047,239), and McKeen et al. (1986) *Phytopathology* 76: 136–139 disclose control of post harvest fruit rot using *B. subtilis.* McKeen et al, supra, have shown that antibiotics similar to the low molecular weight iturin cyclic polypeptides contribute to this fungicidal activity of *B. subtilis.*

Liu et al. (1995) U.S. Pat. No. 5,403,583 disclose a *Bacillus megaterium,* ATCC 55000 and a method to control the fungal plant pathogen, *Rhizoctonia solani.* Islam and Nandi (1985) *Journal of Plant Diseases and Protection* 92(3): 241–246 disclose a *Bacillus megaterium* with antagonism to *Drechslera oryzae,* the causal agent of rice brown spot. The same authors, Islam and Nandi (1985) *Journal of Plant Diseases and Protection* 92(3) 233–240 also disclose in-vitro antagonism of *B. megaterium* against *Drechslera oryzae, Alternaria alternata* and *Fusarium roseum.* They discuss three components in the culture filtrate. The most active antibiotic was highly soluble in water and methanol with a UV peak at 255 nm and a shoulder at 260 nm, which proved to be a polyoxin-like lipopeptide. Cook ((1987) *Proceedings Beltwide Cotton Production—Mechanization Research Conference,* Cotton Council, Memphis, p. 43–45) discloses the use of a suspension of *Bacillus megaterium* to reduce the number of cotton plants killed by *Phymatotrichum omnivorum,* a cause of cotton root rot.

Antibiotic production of *B. megaterium* has been recorded by Berdy (CRC Handbook of Antibiotic Compounds, Vols. I–XIV, (CRC Press, Inc. Boca Raton, Fla. 1980–87) who reports production of low-mammalian toxic peptide antibiotics such as ansamitocin-PDM-O, bacimethrin, megacin, pentapeptide, homopeptides.

Bacilli are known to produce antifungal and antibacterial secondary metabolites (Korzybski et al. (1978)). University of Wisconsin and Cornell researchers have identified a novel fungicidal compound, zwittermicin A, produced by Bacillus sp. (He et al. (1994) Tetra. Lett. 35(16):2499–2502). A second fungicidal metabolite produced by the same strain was recently identified as the known amino-sugar, kanosamine (Milner et al. (1996) Appl. Environ. Microb. 62:3061–3065).

Another group of previously described Bacillus metabolites are the cyclic lipopeptides of the iturin class, some of which are potent fungicidal agents. These agents consist of a cyclic octapeptide with seven α-amino acids and one β-amino acid with an aliphatic side chain. There are several groups of iturins that differ in order and content of the amino acid sequence. These are shown in Table 1 below. Generally, a suite of related molecules is produced with differences in the length and branching of the aliphatic amino acid residue. When tested against Saccharomyces cerevesiae, mycosubtilin was found to be the most active agent (LC50=10 μg/mL) followed by iturin-A and bacillomycin L (both having an LC50=30 μg/mL) (Beeson et al. (1979) J. Antibiotics 32(8):828–833). The mode of action of these cyclic lipopeptides has been reported to be due to interaction with fungal membranes creating transmembrane channels that permit release of vital ions (Latoud et al. (1986) Biochem. Biophys. Acta 856:526–535). Iturin-C is inactive against fungi including Penicillium chrysogenum (Peypoux et al. (1978) Tetrahedron 34:1147–1152).

TABLE 1

Structures of the iturin family of antibiotics

| Antibiotic | L-Asz(X1) | X4 | X5 | X6 | X7 |
|---|---|---|---|---|---|
| Iturin A | L-Asn | L-Gln | L-Pro | D-Asn | L-Ser |
| Iturin C | L-Asp | L-Gln | L-Pro | D-Asn | L-Ser |
| Bacillomycin D | L-Asn | L-Pro | L-Glu | D-Ser | L-Thr |
| Bacillomycin L | L-Asp | L-Ser | L-Gln | D-Ser | L-Thr |
| Bacillomycin F | L-Asn | L-Gln | L-Pro | D-Asn | L-Thr |
| Mycosubtilin | L-Asn | L-Gln | L-Pro | D-Ser | L-Asn |

$R = CH_3, \; CH(CH_3)_2, \; CH_3CH_2\underset{CH_3}{CH}$

A research group at the USDA has investigated the structure/activity relationship of the iturins by synthesizing a number of analogs differing in the amino acid chain length. The researchers reported that the activity of the iturins increased with the length of the fatty acid side chain and the terminal branching in the order iso>normal>anteiso (Bland et al. (1995) Proc. Plant Growth Regulation Soc. Am. 22nd: 105–107). They also state that the "amounts of iturins obtained from natural production are inadequate to be commercially viable" based on their work with a number of iturin producing strains of Bacillus.

Figure 1:
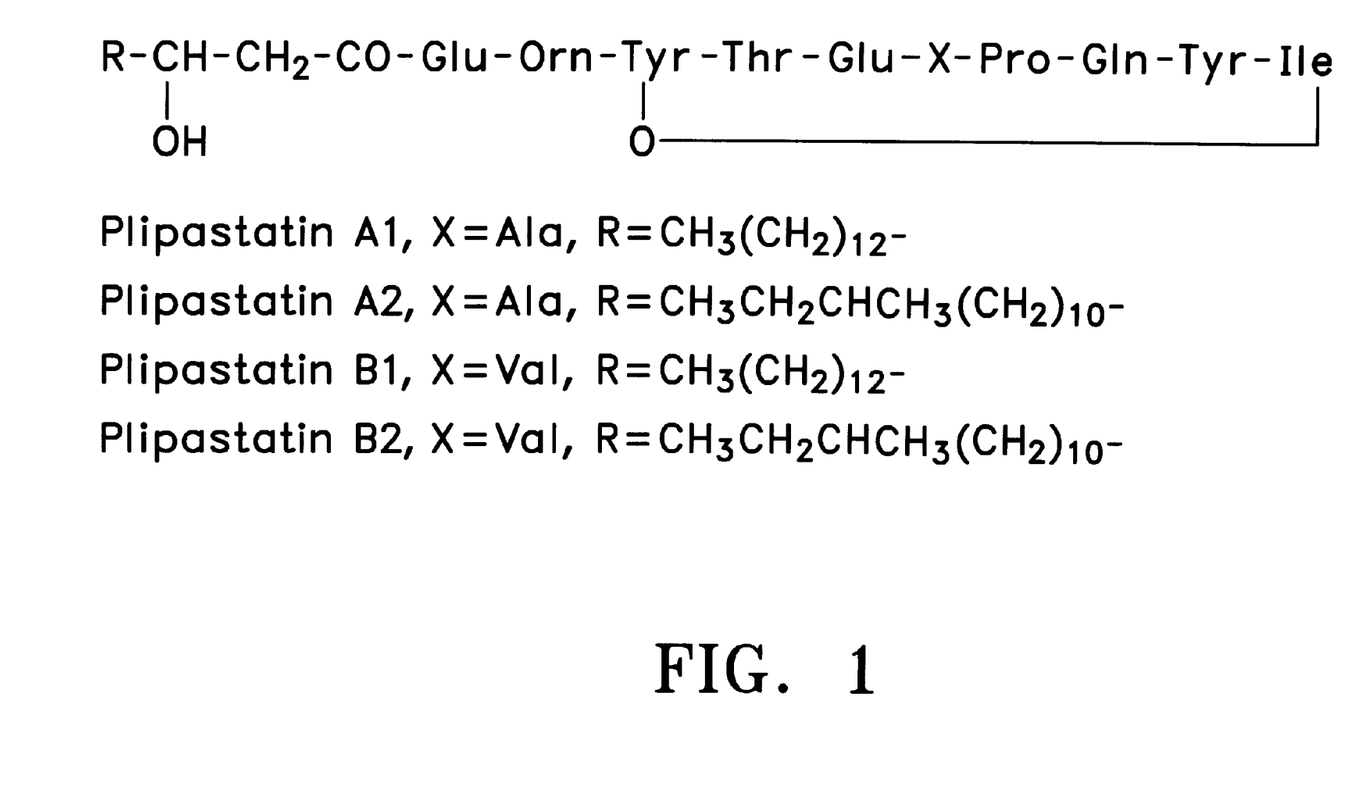
FIG. 1 shows the structure of the plipastatin antibiotics.
Figure 2:
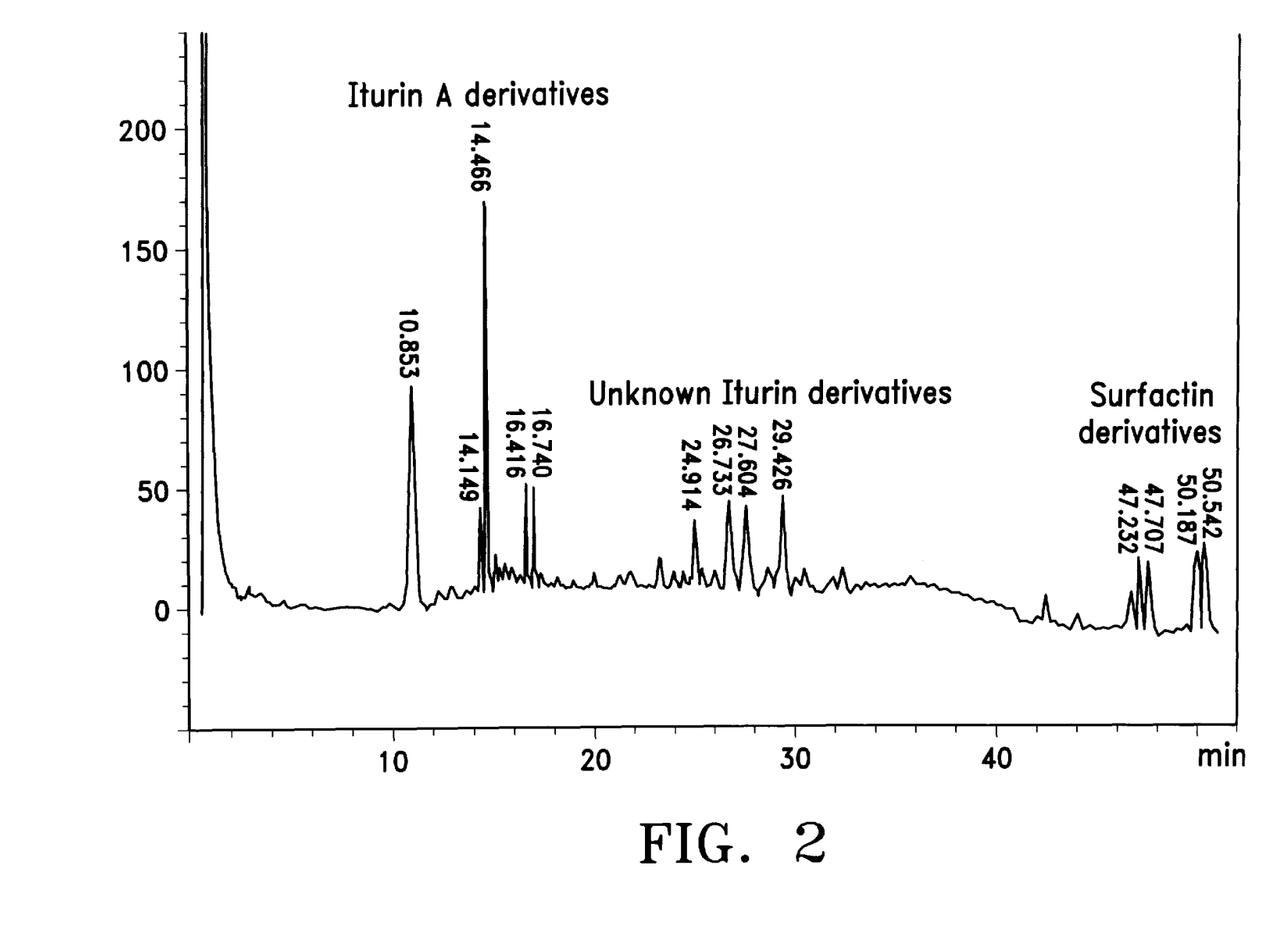
FIG. 2 shows the HPLC chromatogram of AQ713 metabolites.

Another groups of cyclic lipopeptides isolated from B. cereus are the plipastatins. These compounds are a family of acylated decapeptides, the structures of which are shown in FIG. 1 (Nishikiori et al. (1986) J. Antibiotics 39(6): 755–761). These compounds were originally isolated as inhibitors of porcine pancreatic phospholipase $A_2$ (Umezawa et al. (1986) *J. Antibiotics* 39(6):737–744), but were later found to inhibit some plant pathogenic fungi including Botrytis, Pyricularia and Alternaria (Yamada et al. (1990) *Nippon Noyaku Gakkaishi* 15(1):95–96). Yamada also reported a synergistic effect observed between iturin A and the plipastatins, both produced by the same *B. subtilis* strain.

Work has been carried out on fermentation improvements to increase production of the iturins in both liquid (Phae and Shoda (1991) *J. Ferment. Bioeng.* 71:118–121); Ohno et al. (1993) *J. Ferment. Bioeng.* 75:463–465) and solid state fermentations (Ohno et al. (1992) *Biotech. Lett.* 14(9) :817–822; Ohno et al. (1995) *J. Ferment. Bioeng* 5:517–519). There is a report of synergy between the closely related surfactins, that are themselves inactive, and the iturins produced by the same *B. subtilis* strain (Hiraoka et al. (1992) *J. Gen. Appl. Microbiol.* 38:635–640). The nucleotide sequence for the gene that co-regulates biosynthesis of iturin A and surfactin has been published (Huang et al. (1993) *J. Ferment. Bioeng.* 76(6):445–450). Field work on iturin-producing strains has concentrated on soil treatment for control of Rhizoctonia (Asaka and Shoda (1996) *Appl. Environ. Microbiol.* 62:4081–4085) and foliar field applications of iturins have not been reported.

Another cyclic lipopeptide compound produced by *B. subtilis* is surfactin, which possesses an exceptional surfactant activity (Kaninuma et al. (1969) *Agric. Biol. Chem.* 33:973–976). Surfactin contains a C14 or C 15 β-hydroxy fatty acid linked by a lactone ring to a heptapeptide moiety with a LLDLLDL sequence (Arima et al. (1968) *Biochem. Biophys. Res. Commun.* 31:488–494. Sandrin et al. ((1990) *Biotechnol. Appl. Biochem.* 12:370–375) found *B. subtilis* strains that produced both surfactin and iturin A, the bacillomycins F and L and mycosubtilin.

The novel microorganism AQ713 discovered by the inventors, previously thought to be a strain of *Bacillus megaterium* and now identified as a strain of *Bacillus subtilis,* produces A iturins, plipastatins and surfactins. Production of this combination of lipopeptides by a microorganism has not been previously reported. In addition, the inventors have discovered that AQ713 also produces a newly described group of compounds designated as "agrastatins." The combination of all three of the above known compounds with the novel agrastatins is also novel.

One commonly used biopesticide is the gram positive bacterium *Bacillus thuringiensis.* Pesticidal *B. thuringiensis* strains are known to produce crystal proteins during sporulation, which are specifically toxic to certain orders and species of insects and nematodes (See, e.g., U.S. Pat. Nos. 4,999,192 and 5,208,017). Proteinaceous endotoxins produced by *B. thuringiensis* also act as insecticidal agents against corn rootworm and other beetles (e.g., U.S. Pat. No. 5,187,091; Johnson, T.J. et al. (1993), *J. Economic Entomology* 86:330–333). *B. thuringiensis* endotoxins have been shown to be effective as purified crystals, washed cell pellets, and expressed proteins. Warren et al. (WO 96/10083), discloses non-endotoxin proteins produced during the vegetative stage of *Bacillus cereus* and *B. thuringiensis.* These vegetative proteins, called Vip1 and Vip2 have potent activity against corn rootworm (northern and western) (Estruch et al. (1997), *Nature Biotechnology* 15:137–141 and Mullins et al. (1997), *Appl Environ. Microbiol.* 63, (in press).

One *B. thuringiensis* thermostable metabolites, termed beta-exotoxin has also been shown to have pesticidal properties. Burgjeron and Biache (1979), *Entomophaga* 11:279–284 report a beta exotoxin that is active against Colorado potato beetle (*Leptinotarsa decemlineata*). In addition, the known *B. thuringiensis* beta-exotoxins exhibits non-specific pesticidal activity, killing not only nematodes, but also flies, armyworms, mites, and corn rootworms. Sigma exotoxin has a structure similar to beta-exotoxin, and is active against Colorado potato beetle (Argauer et al. (1991) *J. Entomol. Sci.* 26:206–213). Alpha-exotoxin is toxic against larvae of *Musca domestica* (Cluthy (1980) *FEMS Microbiol. Lett.* 8:1–7). Gamma-exotoxins are various proteolytic enzymes, chitinases and proteases. The toxic effects of gamma exotoxins are only expressed in combination with beta-exotoxin or delta-endotoxin. Forsberg et al. (1976) "*Bacillus thuringiensis:* Its effects in Environmental Quality," National Research Council of Canada. Stonard et al. (1994) *ACS Symposium Series* 551: 25 report a water-soluble secondary metabolite active against corn rootworm in the supernatant of a *Bacillus cereus* strain.

There are no documented strains of Bacillus with bacteriacidal, fungicidal and corn rootworm activity. There are no known metabolites produced by *Bacillus subtilis* that are of less than 10,000 molecular weight and are extractable in a non-polar solvent.

DISCLOSURE OF THE INVENTION

A novel antibiotic-producing and metabolite-producing strain of *Bacillus subtilis,* previously identified as *Bacillus megaterium,* is provided that exhibits broad fungicidal and bactericidal activity and also exhibits corn rootworm activity. Also provided is a novel metabolite from the novel *B. subtilis* with activity on corn rootworm. Also provided is a method of treating or protecting plants from fungal and bacterial infections comprising the step of applying an effective amount of the antibiotic-producing *Bacillus subtilis.* The antibiotic-producing *Bacillus subtilis* can be provided as a suspension in a whole broth culture or as an antibiotic-containing supernatant obtained from a whole broth culture of the antibiotic-producing strain of Bacillus. Also provided is a method of treating or protecting plant roots from corn rootworm infestations comprising the step of applying an effective amount of the novel metabolite-producing *Bacillus subtilis.* The novel metabolite-producing *Bacillus subtilis* can be provided as a suspension in a whole broth culture or as a metabolite-containing supernatant or a purified metabolite obtained from a whole broth culture of the microorganism. Also provided are novel compounds, agrastatins, produced by the novel strain AQ713 and a novel combination of compounds comprising inturin A, a plipastatin, a surfactin and an agrastatin.

MODES OF CARRYING OUT THE INVENTION

The present invention provides a novel strain, AQ713, of *Bacillus subtilis,* previously identified as a *Bacillus megaterium,* or mutants thereof with the broad antifungal and antibacterial activity and the novel combination of antifungal and anti-corn rootworm activity. This novel strain is designated AQ713 and was deposited with the NRRL on Mar. 7, 1997 under the provisions of the Budapest Treaty on the International Recognition of the Deposit of Microorganisms for the Purpose of Patent Procedure under Accession No. B21661. The invention also includes methods of preventing and treating fungal and bacterial diseases in plants using such bacterial strains or antibiotic-containing supernatants or pure antibiotics obtained from such bacterial strains. The invention also includes methods of treating plant roots or soil to control corn rootworm larvae with a bacterial suspension of AQ713 or a metabolite-containing supernatant of a culture of AQ713 or purified metabolites from strain AQ713. The invention also includes a solvent-extractable metabolite with activity on corn rootworm with a molecular weight of less than 10,000 daltons. The invention further includes novel compounds, agrastatins, produced by the novel microorganism. Also included is a novel combination comprising an A-type iturin, a plipastatin, a surfactin and an agrastatin.

Definitions

As used herein, "biological control" is defined as control of a pathogen or insect by the use of a second organism. Known mechanisms of biological control include enteric bacteria that control root rot by out-competing fungi for space on the surface of the root. Bacterial toxins, such as antibiotics, have been used to control pathogens. The toxin can be isolated and applied directly to the plant or the bacterial species may administered so it produces the toxin in situ.

The term "fungus" or "fungi" includes a wide variety of nucleated spore-bearing organisms that are devoid of chlorophyll. Examples of fungi include yeasts, molds, mildews, rusts, and mushrooms.

The term "bacteria" includes any prokaryotic organism that does not have a distinct nucleus.

"Fungicidal" means the ability of a substance to increase mortality or inhibit the growth rate of fungi.

"Antibiotic" includes any substance that is able to kill or inhibit a microorganism. Antibiotics may be produced by a microorganism or by a synthetic process or semisynthetic process. The term, therefore, includes a substance that inhibits or kills fungi for example, zwittermicin-A or kanosamine.

"Antifungal" includes any substance that is able to kill or inhibit the growth of fungi.

The term "culturing" refers to the propagation of organisms on or in media of various kinds. "Whole broth culture" refers to a liquid culture containing both cells and media. "Supernatant" refers to the liquid broth remaining when cells grown in broth are removed by centrifugation, filtration, sedimentation, or other means well known in the art.

An "effective amount" is an amount sufficient to effect beneficial or desired results. An effective amount can be administered in one or more administrations. In terms of treatment and protection, an "effective amount" is that amount sufficient to ameliorate, stabilize, reverse, slow or delay progression of the fungal or bacterial disease states.

As used herein, the term "insects" includes all organisms in the class "Insecta." "Pre-adult" insects refers to any form of an organism prior to the adult stage, including, for example, eggs, larvae, and nymphs. "Insecticidal" refers to the ability of a substance to increase mortality or inhibit growth rate of insects. "Nematicidal" refers to the ability of a substance to increase mortality or inhibit the growth rate of nematodes. "Pesticidal" refers to the ability of a substance to increase mortality or inhibit the growth rate of insects, nematodes and mites. "Positive control" means a compound known to have pesticidal activity. "Positive controls" include, but are not limited to commercially available chemical pesticides. The term "negative control" means a compound known not to have pesticidal activity. Examples of negative controls are water or ethyl acetate.

The term "solvent" includes any liquid that holds another substance in solution. "Solvent extractable" refers to any compound that dissolves in a solvent and which then may be isolated from the solvent. Examples of solvents include, but are not limited to, organic solvents like ethyl acetate.

The term "metabolite" refers to any compound, substance or byproduct of a fermentation of a microorganism that has pesticidal activity. Antibiotic as defined above is a metabolite specifically active against a microorganism.

The term "agrastatins" refers to a group of novel compounds having the following structures (SEQ ID NO: 1):

where $R_1$ is a branched or straight aliphatic side chain, C8-C20; X is either Ala or Val; $R_2$ is an acetate or an ester derivative; and Glx is Gln or Glu. These compounds have antibacterial and antifungal activity as well as anti-corn rootworm activity.

We describe a novel metabolite and antibiotic-producing strain of *Bacillus subtilis*, previously identified as *Bacillus megaterium*, that has broad antifungal and antibacterial activity and that also kills or stunts corn rootworm larvae. In another aspect, the present invention provides a method of treating or protecting plants from fungal and bacterial infections comprising applying an effective amount of a supernatant obtained from a whole broth culture of *Bacillus subtilis* AQ713 within the present invention. The supernatant may be obtained well known in the art including centrifugation, filtration, sedimentation and the like.

In another aspect, the invention encompasses a method of treating or protecting plants from fungal and bacterial infections comprising applying an effective amount of the whole broth of the novel strain *Bacillus subtilis*.

In further aspect, the invention encompasses a method of treating or protecting plants from fungal and bacterial diseases comprising applying an effective amount of the antibiotic produced by the novel strain of *Bacillus subtilis*.

In another aspect, the present invention provides a method of treating or protecting plant roots from corn rootworm infestations comprising applying an effective amount of a supernatant obtained from a whole broth culture of *Bacillus subtilis* AQ713 within the present invention. The supernatant may be obtained well known in the art including centrifugation, filtration, sedimentation and the like.

In another aspect, the invention encompasses a method of treating or protecting plants from corn rootworm infestations comprising applying an effective amount of the whole broth of the novel strain *Bacillus subtilis*.

In further aspect, the invention encompasses a method of treating or protecting plant roots from corn rootworm infestations comprising applying an effective amount of the metabolite produced by the novel strain of *Bacillus subtilis*.

In order to achieve good dispersion and adhesion of compositions within the present invention, it may be advantageous to formulate the whole broth culture, supernatant and/or metabolite/antibiotic with components that aid dispersion and adhesion. Suitable formulations will be known to those skilled in the art.

Compositions within the present invention can be formulated as wettable powders, granules and the like, or can be microencapsulated in a suitable medium and the like. Examples of other formulations include, but are not limited to soluble powders, wettable granules, dry flowables, aqueous flowables, wettable dispersible granules, emulsifiable concentrates and aqueous suspensions. Other suitable formulations will be known to those skilled in the art.

In yet a further aspect of the present invention, a novel group of compounds designated "agrastatins" are provided. These compounds exhibit antibacterial and antifungal activity in addition to anti-corn rootworm activity.

In still a further aspect of the present invention, a novel combination comprising an A-type iturin, a plipastatin, a surfactin and an agrastatin is provided.

In another aspect of the present invention, methods of treating or protecting plants from fungal and bacterial diseases comprising applying an effective amount of a novel combination of compounds comprising an A-type iturin, a plipastatin, a surfactin and an agrastatin are provided.

All patents and publications cited herein are hereby incorporated by reference in their entirety. The following examples are provided to illustrate the invention. These examples are not to be construed as limiting.

EXAMPLES

Example 1

Characterization of Strain AQ713

The isolate was identified based on utilization of the Biolog microplate panel (Biolog, Inc., Hayward, Calif.) as described in Bochner (1989) *Nature* 339: 157–158. The Biolog microplate is comprised of prefilled and dried panel wells with 95 different carbon substrates plates available for gram positive and gram negative bacteria. The isolate was grown in liquid medium at 28° C. and after 24 hrs a washed cell suspension (0.85% saline) was inoculated into each panel well of a GP Microplate (Biolog, Inc.) After 24 hrs at 28° C., carbon utilization reactions were assessed. Substrate utilization profiles were then compared to the Biolog Gram-Positive Data Base (release 3.50) and isolated to closest similar species. Biolog results gave a similarity index of 0.883 to *Bacillus megaterium*.

A more extensive characterization of AQ713 was conducted by the American Type Culture Collection, Rockville, Md.

Isolate submitted as: Unknown; Strain AQ 713
Isolate identified as: Using the available physiological and biochemical data, this strain most closely resembles *Bacillus subtilis*.
Cellular morphology: The motile cells are found in singly, with one endospore formed in the central or subterminal region. The cells are uniformly stained Gram positive.
Colonial morphology: The colonies are opaque and irregular with convex elevation, a rough, dull surface and an erose margin.

Characterization Data of Strain AQ 713:

| | | | |
|---|---|---|---|
| Rods | + | Colony opaque | + |
| Rods straight | + | Colony entire | – |
| Rods curved | – | Colony erose | + |
| Cells single | + | Colony lobate | – |
| Cells chained | – | Colony circular | – |
| Ends tapered | – | Colony irregular | + |
| Ends rounded | + | Colony rhizoid | – |
| Ends squared | – | Colony low convex | + |
| Endospore formed | + | Colony high convex | – |
| Sporangium swollen | – | Colony flat | – |

-continued

| | | | |
|---|---|---|---|
| One spore/cell | + | Colony raised | − |
| Spore round | − | Colony glistening | − |
| Spore cylindrical | + | Colony dull | + |
| Spore oval | + | Colony dry | − |
| Spore central | + | Colony smooth | − |
| Spore terminal | − | Colony rough | + |
| Spore subterminal | + | Soluble brown pigment | − |
| Gram stained | + | Soluble black pigment | − |
| Gram positive | + | Soluble yellow pigment | − |
| Gram negative | − | Insoluble brown pigment | − |
| Gram variable | − | Insoluble black pigment | − |
| Vacuoles present | − | Insoluble yellow pigment | − |
| Colony translucent | − | Insoluble orange pigment | − |
| Colony transparent | − | Insoluble red pigment | − |
| Cells motile | + | Acid from lactose | − |
| Growth at 15° C. | + | Gas from lactose | − |
| Growth at 20° C. | + | Acid from mannitol | − |
| Growth at 26° C. | + | Gas from mannitol | − |
| Growth at 30° C. | + | Acid from mannose | − |
| Growth at 37° C. | + | Gas from mannose | − |
| Growth at 45° C. | + | Acid from sucrose | weak |
| Growth at 50° C. | weak | Acid delayed > 14 days | weak |
| Growth at 55° C. | − | Gas from sucrose | − |
| Growth at 60° C. | − | Acid from trehalose | − |
| Growth at 65° C. | − | Gas from trehalose | − |
| Catalase | + | Acid from xylose | − |
| Oxidase | + | Gas from xylose | − |
| Casein hydrolysis | + | Aerobe | − |
| Gelatin liquification | + | Facultative | − |
| Hippurate hydrolysis | − | Microaerophile | + |
| Lecithinase degradation | − | Anaerobe | − |
| Starch hydrolysis | + | Gas from sealed nitrate | − |
| Tween 80 hydrolysis | + | Gas from sealed glucose | − |
| Tyrosine decomposition | − | Indole | − |
| Growth in 2% NaCl | + | Nitrate to nitrite | + |
| Growth in 5% NaCl | + | Nitrate to gas | − |
| Growth in 7% NaCl | + | Methylene blue reduction | + |
| Growth in 10% NaCl | + | Methylene blue reoxidation | − |
| Growth in 0.2% Na azide | V | Litmus milk acid | − |
| Growth at pH 4.5 | + | Litmus milk coagulated | − |
| Growth at pH 6.0 | + | Litmus milk alkaline | + |
| Acid from arabinose | − | Litmus milk reduced | + |
| Gas from arabinose | − | Litmus Milk peptonized | + |
| Acid from cellobiose | weak | VP (5198) positive | + |
| Acid delayed > 14 days | weak | VP (5331) positive | + |
| Gas from cellobiose | − | pH VP 5198 6.0 or less | − |
| Acid from fructose | + | pH VP 5198 6.5–7.5 | + |
| Acid delayed > 14 days | − | pH VP 5198 8.0 or more | − |
| Gas from fructose | − | Citrate utilization | + |
| Acid from glucose | + | Propionate utilization | − |
| Acid delayed > 14 days | − | Phenylalanine deamination | − |
| Gas from glucose | − | | |

Comments: Using the available physiological and biochemical data, this strain most closely resembles *Bacillus subtilis*.

| Key Characterization Results | | |
|---|---|---|
| Characterization Tests | Strain AQ713 | *Bacillus subtilis* |
| Swollen sporangium | − | − |
| Anaerobic growth | microaerophilic | microaerophilic |
| VP reaction | + | + |
| pH of VP | 7.0 | 5.0–8.0 |
| Maximum temperature growth | 55° C. | 45–55° C. |
| 7% NaCl growth | + | + |
| Acid from glucose | + | + |
| Acid from arabinose | − | + |
| Acid from xylose | − | + |
| Acid from mannitol | − | + |
| Casein decomposition | + | + |
| Tyrosine decomposition | − | − |
| Citrate utilization | + | + |
| Propionate utilization | − | − |

Reference:

Gordon, R-E., W. C. Haynes and C. H. N. Pang. 1973. The Genus Bacillus. Handbook No. 427. U.S. Department of Agriculture, Washington, D.C.

EXAMPLE 2

Activity of AQ713 Against Corn Rootworm

Bacillus samples were grown in a Bacillus culture media. Medium 2 contained 5% peptone, 5% dextrose, 3% yeast extract, 3% malt extract, 1.5% proflo cotton seed extract (59% protein, 4.26% fat, 6.73% ash, 3.19% fiber and trace amounts of gossypol; the balance is water), 10% soy flour, and 0.5 % $MgSO_4 \times 7H_2O$. Medium 3 contained the same ingredients, except with 20% peptone and 3.4% $KH_2PO_4$ and 4.3% $K_2HPO_4$. One day old streaked cultures were used to inoculate 250 mL baffled shake flasks. Flasks were shaken at 200 rpm at 29° C. for 5 days. To assay insecticidal activity, 35 mL of culture broth were centrifuged at 5,200 rpm for 20 minutes and the supernatant used in microassay described below.

Assays were performed in 96-well microplates. Each well contained a solid agar substrate, a test organism and either a positive control, a negative control or supernatant obtained as described in Example 1 from the novel Bacillus strain.

To assay insecticidal activity, an agar substrate was prepared for the wells of the microplate according to Marrone et al. (1985), *J. Econ. Entomol.* 78: 290–293. To assay nematicidal activity, plain agar (1.5%) was used in the wells instead.

A 1 ppm solution of Avid® (avermectin) was used as a positive control. Deionized water was used as a negative control. Two replicates of test sample or control were used for each assay. 40 uL of supernatant sample or whole broth grown in medium 1, 2 or 3 were dispensed into each sample well. Plates were then placed in a fume hood to dry for approximately 2–3 hours until the agar solution was dried.

Test organisms were either pre-adult corn rootworms (*Diabrotica undecimpunctata*), pre-adult German cockroaches (*Blatella germanica*), pre-adult beet armyworms (*Spodoptera exigua*), pre-adult flies (*Drosophila melanogaster*), or the N2 strain of the nematode *Caenorhabditis elegans*. Test organisms were diluted in 0. 1% agar to a concentration of approximately 5 organisms per 25 uL of agar dispensed into each well. The microplate was sealed with an airtight substance such as Mylar®, and each well ventilated with a pin press. The plates were incubated at 27° C. for up to 7 days.

After incubation, wells were scored by noting neonate mortality or the degree of larval development. Sample wells containing all dead or stunted larvae were given a score of 1, wells containing some dead and other severely stunted larvae were given a score of 2, live but stunted larvae were scored as 3 and sample wells containing no dead larvae were given a score of 4. Scores were averaged among replicates within each sample. Results are summarized in Tables 2 and 3.

TABLE 2

Score Rating of AQ713 Against Insect Pests Whole broth

| | C. elegans | Corn rootworm | Beet armyworm | Fruit Fly | Positive Control | Negative Control |
|---|---|---|---|---|---|---|
| Medium 2 | NT | 1.0 | 4.0 | 4.0 | 1.0 | 4.0 |
| Medium 3 | NT | 2.0 | 4.0 | 4.0 | 1.0 | 4.0 |

NT = not tested

TABLE 3

Score Rating of AQ713 Against Insect Pests Supernatant

| | C. elegans | Corn rootworm | Beet armyworm | Fruit Fly | German Cockroach | Positive Control | Negative Control |
|---|---|---|---|---|---|---|---|
| Medium 2 | 4.0 | 3.0 | 4.0 | 4.0 | 4.0 | 1.0 | 4.0 |
| Medium 2 | 4.0 | 4.0 | 4.0 | 4.0 | 4.0 | 1.0 | 4.0 |

These tests show that AQ713 was active in both media as a whole broth culture, with the best activity in medium 2. The supernatant was only active when AQ713 was grown in medium 2.

EXAMPLE 3

Chemical Properties of the AQ713 Metabolite Active Against Corn Rootworm 50 mL of AQ713 was grown in media 2. To each culture was added 50 mL ethyl acetate and the mixture was shaken in a separatory funnel for 2 minutes. The aqueous layer was removed and the organic layer was collected in a bottle containing magnesium sulfate. The organic filtrate was then filtered into a round bottom flask and the solvent removed on the rotovap.

For the bioassay, the dried organic extract was redissolved in 2.5 mL acetone. A 40 uL aliquot was removed and diluted to 800 uL with 70% acetone/water. This is a 10X concentration of the organic extract. Serial dilutions were carried out to obtain samples on neonate corn rootworm with percent mortality recorded of neonate larvae (1 per well in a microtiter plate as prepared above) after 7 days. The results are recorded in Table 4.

TABLE 4

Activity of Ethyl Acetate Extracts of AQ713 Against Corn Rootworm

| Sample | | Percent Mortality |
|---|---|---|
| AQ713: | Organic extract 10× | 89 |
| | Organic extract 5× | 93 |
| | Organic extract 1× | 65 |
| | Wholebroth | 100 |
| | 70% acetone/water | 27 |
| | Water | 59 |

The results show that AQ713 produces a solvent-extractable metabolite that kills corn rootworms.

To determine the molecular weight range of the active metabolite, a 50-mL culture of AQ713 was grown in media 2. One mL was placed into a microfuge tube and spun at 12,000 rpm for 15 minutes. The supernatant was removed. 500 microliters of supernatant was placed on top of a 10,000 dalton molecular weight centricon filter. These were centrifuged according to the manufacturer's instructions (12,000 rpm for 35 minutes). The filtrate was collected and the retentate recovered by centrifugation and washing of the filter. Samples of the supernatant, filtrate and retentate were tested against neonate corn rootworm larvae (96 well-plate with insect diet, Marrone et al., supra as above; 40 uL of sample per well and 8 wells for each sample, 1 larva/well). The results of the test are shown in Table 5.

TABLE 5

Molecular Weight Cutoff of AQ713
Percent Mortality
Against Corn Rootworm

| AQ713: | supernatant | 43 |
|---|---|---|
| | filtrate | 63 |
| | retentate | 17 |

The results show that the supernatant and filtrate were active, thus the molecular weight of the metabolite is less than 10,000 daltons.

EXAMPLE 4

Chemical properties of the AQ713 metabolite active against plant pathogens 50 mL of AQ713 was grown in media 2. To each culture was added 50 mL ethyl acetate and the mixture was shaken in a separatory funnel for 2 minutes. The aqueous layer was removed and the organic layer was collected in a bottle containing magnesium sulfate. The organic filtrate was then filtered into a round bottom flask and the solvent removed on the rotovap.

For the bioassay, the dried organic extract was redissolved in 2.5 mL acetone. A 40 uL aliquot was removed and diluted to 800 uL with 70% acetone/water. This is a 10X concentration of the organic extract. A 96-well plate assay (described below) plant pathogen assay with *Pythium ultimum* and *Botrytis cinerea* was conducted to determine activity of the organic extract. The whole broth gave 100% control (score of 1), but the 10X organic extract gave no control of the two plant pathogens (score of 4). This indicates that the active antibiotics, unlike the corn rootworm active metabolites produced by AQ713 are not extractable in an organic solvent such as ethyl acetate.

Further testing provided for the isolation of a novel compound, agrastatin A. A butanol extract was made of the fermentation broth by first extracting the broth two times with an equal volume of ethyl acetate and separating the layers. The aqueous fraction was then extracted two times with an equal volume of butanol. The butanol extracts were combined and solvent was removed with a rotary evaporator. A powder was obtained by freeze drying the resulting extract.

The powder was dissolved in 80% acetonitrile/water and sonicated. The solution was applied to a C-18 solid phase extraction (SPE) cartridge that had been activated with methanol and equilibrated with 80% acetonitrile/water. The SPE cartridge was eluted with 80% ACN/water and this eluent was collected and the solvents removed. The eluent was further purified by HPLC. A C-18 HPLC column (1 cm×25 cm) was used (UV detection at 210 nm) with an acetonitrile +0.05% TFA/water +0.05% TFA solvent gradient as follows: 0–20 minutes, 33% ACN; 20–30 minutes, 40% ACN; 30–45 minutes, 45–55% ACN; and 45–63 minutes, 55% ACN.

An HPLC chromatogram of AQ713 shows the presence of the iturins, iturin-like compounds (plipastatins and agrastatins) and surfactins, see FIG. 1. Iturins A2, A3, A4, A7 and A6 were identified by a combination of NMR data and LC mass spectrometry data and comparison to literature values. Surfactins were identified by comparison to purchased surfactin standards by HPLC and by LC mass spectrometry.

The iturin-like compounds were determined to be a mixture of plipastatins and the novel agrastatins by a combination of amino acid analysis and LC mass spectrometry. Extensive NMR data was also collected for one of the novel compounds (HPLC peak 20), designated agrastatin A. Agrastatin A was found to contain the following amino acids: Thr; 3 Glu; Pro; Ala; Val; 2 Tyr; and Orn. This make up differs from plipastatin A by the presence of Val and the loss of Ile. The molecular weight of agrastatin A was determined to be 1448 which corresponds to the following structure (SEQ ID NO: 2):

The straight chain nature of the fatty acid portion was confirmed by $^1$H NMR. The position of the amino acids in the cyclic peptide was determined by detailed analysis of the TOCSY and ROESY datasets.

Mass spectrometry and amino acid analysis of agrastatin B (HPLC peak 26) suggest that its structure is similar to plipastatin B2 with the substitution of the Ala residue with Val. The structure is shown below (SEQ ID NO: 3):

TABLE 6

In-Vitro Inhibition of Fungal Growth (96-well plate)

|  | Media 2 Score | Media 3 Score |
|---|---|---|
| AQ713 Supernatant |  |  |
| Phytophthora infestans | 1 | 1 |
| Pythium ultimum | 1 | 1 |
| Botrytis cinerea | 1 | 1 |
| Rhizoctonia solani | 4 | 1 |
| Alternaria solani | 1 | 1 |
| AQ713 Whole broth |  |  |
| Colletotrichum cocodes | 1 | NT |
| Alternaria brassicicola | 1 | NT |
| Botrytis cinerea | 1 | NT |
| Cladosporium cucumerinum | 1 | NT |
| Monilinia fructicola | 1 | NT |
| Venturia pyrina | 1 | NT |
| Rhizoctonia solani | 1 | NT |
| Alternaria solani | 1 | NT |

NT Not tested

The results show that AQ713 has broad fungicidal spectrum in-vitro and that both the whole broth and supernatant are highly active. The supernatant was active on *Rhizoctonia solani* in medium 3 but not medium 2.

EXAMPLE 5

Activity of AQ713 Against Plant Pathogens in in-vitro Culture (96-well plate)

To determine if AQ713 is effective against the fungi, *Phytophthora infestans, Pythium ultimum, Botrytis cinerea, Rhizoctonia solani, Alternaria solani,* the following experiments were performed. 96-well plates (flat-bottomed, 400 microliters per well, Nunc brand) were filled with an agar medium (potato dextrose agar) (PDA, Difco). *Phytophthora infestans* cultures were grown for three days in liquid YPG-1 medium (0.4 g yeast, 0.1% KH$_2$PO, 0.5% MgSO$_4$X 7 H$_2$O, 1.5% glucose). For the other fungi, spores were scraped from the surface of petri plates and 0.1–0.2 mL aliquots of deionized water and spore suspension (concentration approximately 2×10$^6$ spores/mL) of pathogen were spread onto the agar.

AQ713 was grown for 72 hours in the medium 2 or 3 as described in Example 2. To obtain supernatants, the whole broth culture was centrifuged at 5,200 rpm for 20 minutes. The fungal plant pathogens were pipetted onto the 96-well plates (8 wells/pathogen). The presence or absence of fungal growth was recorded for each of 8 wells. Approximately 40 uL of AQ713 supernatant or 20 uL of whole broth was added to each well. A score of "1" means complete inhibition of fungal growth. A score of "4" means no inhibition of fungal growth. Results are shown in Table 6.

EXAMPLE 6

Activity of AQ713 Against Plant Pathogens in in-vitro Culture (zone assay)

To determine the activity of AQ713 in an agar diffusion (zone) assay, plant pathogen spores were spread over the surface of potato dextrose agar in 10 cm petri dishes. 7.0 mm wells were removed from the agar and a 100 uL sample of the supernatant of AQ713 grown in medium 2 was placed in the well. Supernatant was prepared by centrifuging at 4200 rpm for 40 minutes. The supernatant was then spun again at 4200 rpm for another 40 minutes. Typical results consisted of a zone of no growth and/or reduced growth of the pathogen around the well. The zone size in millimeters was measured and recorded. The results are shown in Table 7.

TABLE 7

In-Vitro Inhibition of Fungal Plant Pathogen Growth (Zone Test)

|  | Alternaria brassicicola | Botrytis cinerea | Monilinia fructicola |
|---|---|---|---|
| AQ713 supernatant Zone size (mm) | 16 | 23 | 14 |
| AQ713 Whole broth | 22 | 15 | 18 |

EXAMPLE 7

Activity of AQ713 Against Bacterial Plant Pathogens

A standard agar diffusion assay was set up as in example 6. A lawn of each bacterial pathogen was spread over the surface of a petri plate. 100 uL of AQ713 whole broth grown in medium 2 was placed in each well. The size of the zone was measured in millimeters.

TABLE 8

In-Vitro Inhibition of Bacterial Plant Pathogens (Zone Test)

| AQ713 Whole broth: | Inhibition Zone (mm) |
|---|---|
| *Acidovorax avenae* subsp. *citrulli* | 18 |
| *Pseudomonas syringae* pv. tomato | 11 |
| *Xanthomonas campestris* pv. campestris | 18 |
| *Erwinia carotovora* subsp. *carotovora* | 11 |
| *Clavibacter michiganense* subsp. *michiganense* | 22 |

AQ713 was active against all species of bacterial plant pathogens tested in-vitro.

EXAMPLE 8

Activity of AQ713 Against Plant Pathogens in Plant Tests

The activity of AQ713 was tested against gray mold, *Botrytis cinerea*, on beans and geranium leaves, *Alternaria solani* on tomato seedlings, and downy mildew of lettuce, *Bremia lactucae*.

For *A. solani*, tomato seedlings at the 2–3 leaf stage planted in 6-packs were sprayed to runoff with AQ713 whole broth (media 2). After spraying, the seedlings were allowed to dry (about 1.5 hours). The seedlings were then sprayed with $5.0 \times 10^4$ spores/mL. Seedlings were covered with a plastic dome and kept at 28° C. in a Percival incubator. Water with no AQ713, with and without spores of the pathogen was used as a negative control and a positive pathogen control. Four days later the test was read. On the water *A. solani* control, there were uniform lesions over all the leaves and the cotyledons were detached and severely infected (rating of 5=complete infection, no control). AQ713 treated plants had a few light lesions scattered on the true leaves. The cotyledons were attached but with some small lesions (rating of 1). The negative control was not infected.

A second test was set up using detached tomato seedlings (stems broken off at the ground level) placed in mason jars filled with water put under domes and stored as above. The plants were sprayed as above and the symptoms of *A. solani* were recorded four days later. There were no symptoms on the negative control. On the positive control, there were uniform lesions over the seedlings. The AQ713 treatment was rated 1 (few or no lesions). Two days later, the plants in the positive control were destroyed, but the AQ713 treated seedlings were virtually clean and looked the same as the negative controls (water sprayed plants).

For the test on *Botrytis cinerea*, the first true leaves of a bean plant were wounded by pressing the mouth of a 13×100 culture tube onto each leaf. Each leaf received two wounds/ leaf. The leaves were sprayed with AQ713 whole broth (media 2) or water alone or the pathogen alone. When dry, they were again sprayed with *B. cinerea* spores ($0.8 \times 10^6$ spores/mL). The leaves were placed in flats covered with plastic domes and stored at 18–20° C. in a Percival incubator. Five days later, the positive control (pathogen alone) was rotted in an area about 25 mm in diameter. The negative control (water alone) had no rotting. AQ713 showed no infections on 7 of 8 circles where the leaves were wounded. The one that was infected had light infection at two locations around the circle.

For the Bremia test, lettuce seeds were planted in a layer of sterilized potting mix containing peat, perlite and vermiculite in small clear plastic plant condominiums about 8 centimeters high and wide. After the lettuce germinated (one week), the lettuce seedlings were sprayed with the AQ713 broth or supernatant sample. The plants were allowed to dry and then downy mildew spore suspension from infected lettuce seedlings was sprayed onto the seedlings. The plastic covers were placed over the plants and incubated at 18–20 20° C. in a Percival incubator. One week later, the test was evaluated. AQ713 did not prevent downy mildew from Bremia on lettuce seedlings.

EXAMPLE 9

Efficacy of AQ713 Against Plant Diseases (Greenhouse Test)

Grape Downy Mildew

AQ713 was grown in a soy-based medium in a 400 liter fermenter for 48 hours. Grape plants (cultivar Chardonnay) were sprayed with a hand-held sprayer to run-off with whole broth from the 400 liter fermentation run diluted with sterile water to 0.5 X and 0.25 X concentrations. When the foliage dried, the plants were sprayed a second time. After drying, the plants were inoculated with the pathogen causing grape downy mildew, *Plasmopara viticola*. Three plants were treated for each dose. Each plant was evaluated by estimating the percent disease control based on a scale from 0 to 100% control. 100% control is a plant with no visible lesions. A chemical fungicide, metalaxyl, was used for comparison. The results were as follows:

| AQ713 0.5× whole broth | 97.7% control |
|---|---|
| AQ713 0.25× whole broth | 100% control |
| Metalaxyl 30 ppm | 100% control |
| Metalaxyl 10 ppm | 98.3% control |
| Metalaxyl 1 ppm | 80% control |

The results demonstrate that AQ713 effected control of grape downy mildew as well as the chemical fungicide.

EXAMPLE 10

Efficacy of AQ713 Against Squash Powdery Mildew

AQ713 was grown in a soy-based medium in a 400 liter fermenter for 48 hours. Squash plants (Crookneck and Acorn) were sprayed with a hand-held sprayer to run-off with whole broth from the 400 liter fermentation run and a sample diluted with sterile water to 0.5X concentration. After drying, the plants were inoculated with the squash powdery mildew pathogen, *Sphaerotheca fuliginea*. Two plants were treated for each dose. Spray dried powder of the whole broth was also tested. The 400 liter fermentation broth was spray dried to remove the water. 10% and 2.5% spray dried powder solutions were sprayed on the plants to run-off as above. The incidence of powdery mildew disease was rated on a score from 0 to 5. The 5 rating is 100% disease whereas the 0 rating is no disease. The results are shown below in Table 9.

TABLE 9

| Test Suspension | Acorn Squash Plant 1 | Acorn Squash Plant 2 | Crookneck Squash Plant 1 | Crookneck Squash Plant 2 |
|---|---|---|---|---|
| AQ713 1× whole broth | 0 | 0 | 0 | 0 |
| AQ713 0.5× whole broth | 0 | 0 | 0 | 0 |
| AQ713 10% spray dried powder | 0 | 0 | 0 | 0 |
| AQ713 2.5% spray dried powder | 0 | 0 | 0.5 | 1 |

AQ713 whole broth and spray dried powder provided nearly complete control of squash powdery mildew.

EXAMPLE 11

Efficacy of AQ713 on Late Blight, Gray Mold, Grape Powdery Mildew, Cereal Powdery Mildew, Sheath Blight and Rice Blast in the Greenhouse AQ713 was grown in a soy-based medium for 72 hours in a 250 mL shake flask. The disease, causative pathogen and host are listed in Table 10 below. This whole broth culture was tested on the plants as shown in Table 11 below.

TABLE 10

| Disease | Plant Pathogen | Host |
|---|---|---|
| Late Blight | Phytophthora infestans | Tomato |
| Gray Mold | Botrytis cinerea | Pepper |
| Sheath Blight | Rhizoctonia solani | Rice |
| Rice Blast | Pyricularia oryzae | Rice |
| Powdery Mildew | Uncinula necator | Grape |
| Powdery Mildew | Drysiphe graminis f. sp. graminis | Wheat |

Each broth was sprayed to run-off at 1X concentration on the test plants with a hand held sprayer, allowed to dry and then sprayed a second time. Three plants were treated for each disease and treatment. After drying, the plants were inoculated with the pathogens. Each plant was evaluated by estimating the percent disease control based on a scale from 0 to 100% control 100% control refers to a plant with no visible lesions. Chemical fungicides were used for comparison. Disease index is the severity of the disease on the untreated control.

TABLE 11

| | P. infestans | B. cinerea | E. graminis | U. necator | P. oryzae | R. solani |
|---|---|---|---|---|---|---|
| AQ713 | 70 | 100 | 84 | 100 | 100 | 100 |
| Metalaxy 30 ppm | 100 | | | | | |
| Metalaxyl 10 ppm | 77 | | | | | |
| Propiconazole 10 ppm | | 87 | | | | |
| Propiconazole 5 ppm | | 57 | | | | |
| Propiconazole 0.5 ppm | | | 100 | | | |

TABLE 11-continued

| | P. infestans | B. cinerea | E. graminis | U. necator | P. oryzae | R. solani |
|---|---|---|---|---|---|---|
| Propiconazole 0.2 ppm | | | 54 | | | |
| Myclobutanil 30 ppm | | | | 100 | | |
| Myclobutanil 10 ppm | | | | 100 | | |
| Pencycuron 50 ppm | | | | | 100 | |
| Pencycuron 10 ppm | | | | | 100 | |
| Benomyl 100 ppm | | | | | | 100 |
| Benomyl 40 ppm | | | | | | 77 |
| Disease Index (%) | 80 | 95 | 70 | 50 | 60 | 80 |

AQ713 showed activity that was equivalent to chemical fungicides on all the pathogens tested.

EXAMPLE 12

Efficacy of AQ713 Against Brassica Downy Mildew

Bacillus strain AQ713 was grown in a ten liter fermenter in a soy-based medium for 48 hours. The whole broth culture at 1X strength was sprayed onto three week-old cauliflower and brussel sprouts plants at the full cotyledon stage with an artist's air brush powered by compressed air. Three replicates of 15–25 seedlings/pot were sprayed per treatment. Quadris™, an azoxystrobin fungicide from Zeneca, was also sprayed on plants (three per treatment) at rates of 250 ppm and 125 ppm. A spore suspension of downy mildew, Peronospora parasitica, at $1-5 \times 10^4$ spores/mL was sprayed onto the Brassica plants after the AQ713 and Quadris sprays dried. The plants were held at 15–17° C. for 24 hours for infection, then the seedlings were incubated at 20–24° C. for six days. The pots were returned to 15–17° C. overnight to allow sporulation of the pathogen until the test was rated. Each plant was evaluated by estimating the percent disease control based on a scale from 0 to 100% control. 100% control is a plant with no sporulating lesions. The results averaged across replicate pots are shown below in Table 12.

TABLE 12

| | Reading taken December 23 | Reading taken December 30 | Reading taken January 6 |
|---|---|---|---|
| AQ713 whole broth | 100 | 90 | 75 |
| Quadris 250 ppm | 100 | NT | NT |
| Quadris 125 ppm | NT | 100 | 100 |
| Water Control | 0 | 0 | 0 |

NT = Not Tested

AQ713 controlled downy mildew effectively for three weeks in duration.

EXAMPLE 13

Synergism of AQ713 and a Commercial Fungicide

AQ713 was grown in a ten liter fermenter in a soy-based medium for 72 hours. The bacterial culture was diluted with sterile water to 0.5X and 0.25X concentrations. The culture at 1X, 0.5X and 0.25X concentrations was sprayed onto three week-old pepper plants with an artist's air brush powered by compressed air. Three plants were sprayed per treatment. Quadris™, an azoxystrobin fungicide from Zeneca, was also sprayed on plants (three per treatment) at concentrations of 500 ppm, 250 ppm and 125 ppm. In addition, combinations of Quadris plus the whole broth culture of AQ713 in a 1:1 ratio were sprayed onto pepper plants (three per treatment). The treatments with and without Quadris are outlined in Table 13 below. A spore suspension of *Botrytis cinerea,* gray mold, at $1 \times 10^6$ spores/mL was sprayed onto the pepper plants after the AQ713 and Quadris sprays dried. The plants were held at 20–22° C. for 3 days until the test was rated. The incidence of gray mold disease was rated on a score from 0 to 5. The 5 rating indicates 100% disease whereas the 0 rating indicates no disease. The results are shown in Table 13 below.

TABLE 13

| Treatment | Rating Replicate 1 | Rating Replicate 2 | Rating Replicate 3 | Rating Average |
| --- | --- | --- | --- | --- |
| AQ713 1× | 0.5 | 0.5 | 1.5 | 0.8 |
| AQ713 0.5× | 2.0 | 2.5 | 2.0 | 2.2 |
| AQ713 0.25× | 3.0 | 3.0 | 2.0 | 2.7 |
| Quadris 500 ppm | 4.0 | 3.5 | 4.0 | 3.8 |
| Quadris 250 ppm | 2.5 | 3.5 | 3.0 | 3.0 |
| AQ713 1× + Quadris 500 ppm | 0.5 | 1.0 | 1.0 | 0.8 |
| AQ713 1× + Quadris 250 ppm | 1.0 | 1.0 | 0.5 | 0.8 |
| AQ713 0.5× + Quadris 250 ppm | 0.5 | 1.0 | 1.0 | 0.8 |
| AQ713 0.25× + Quadris 250 ppm | 0.5 | 1.0 | 2.5 | 1.3 |
| Water control | 4.0 | 5.0 | 5.0 | 4.7 |
| Water control 2 | 5.0 | 5.0 | 5.0 | 5.0 |

The results clearly show that combinations of Quadris and AQ713 control gray mold disease significantly better than either Quadris or AQ713 alone.

What is claimed is:

1. A biologically pure culture of *Bacillus subtilis* strain AQ713, NRRL Accession No. B21661 and mutants thereof having all the identifying characteristics of said strain.

2. A metabolite produced by the *Bacillus subtilis* strain of claim 1 that exhibits activity against corn rootworm, is solvent extractable and has a molecular weight of less than 10,000 daltons.

3. A supernatant obtained from a culture of the *Bacillus subtilis* strain AQ713 of claim 1 that exhibits antifungal and antibacterial activity and activity against corn rootworm.

4. A composition comprising the whole broth culture of the *Bacillus subtilis* strain AQ713 of claim 1 and a chemical fungicide.

5. A composition comprising the whole broth culture of the *Bacillus subtilis* strain AQ713 of claim 1 and a biological or chemical pesticide.

6. The composition of claim 5 further comprising a chemical fungicide.

7. A composition comprising the metabolite of claim 2 and a chemical fungicide.

8. A composition comprising the metabolite of claim 2 and a biological or chemical pesticide.

9. The composition of claim 8 further comprising chemical fungicide.

10. A composition comprising the supernatant of claim 3 and a chemical fungicide.

11. A composition comprising the supernatant of claim 3 and a biological or chemical pesticide.

12. The composition of claim 11 further comprising a chemical pesticide.

13. A method for protecting or treating plants and fruit from fungal and bacterial infections and corn rootworm infestations comprising applying an effective amount of the *Bacillus subtilis* strain of claim 1.

14. A method for protecting or treating plants and fruit from fungal and bacterial infections and corn rootworm infestations comprising applying an effective amount of the metabolite of claim 2.

15. A method for protecting or treating plants and fruit from fungal and bacterial infections and corn rootworm infestations comprising applying an effective amount of the supernatant of claim 3.

16. A method for protecting or treating plants and fruit from fungal and bacterial infections and corn rootworm infestations comprising applying an effective amount of the composition of claim 4, 5, 6, 7, 8, 9, 10, 11, or 12.

17. The method of claim 13, 14 or 15 wherein the infections are caused by at least one microorganism selected from the group consisting of *Phytophthora infestans, Rhizoctonia solani, Pythium ultimum, Botrytis cinerea, Alternaria solani, Colletotrichum cocodes, Alternaria brassicicola, Cladosporium cucumerinum, Monilinia fructicola, Venturia pyrina, Acidovorax avenae, Pseudomonas syringae, Xanthomonas campestris, Erwinia carotovora, Clavibacter michiganense, Plasmopara viticola, Sphaerotheca fuliginea, Uncinula necator,* and *Peronospora parasitica*.

18. The method of claim 16 wherein the infections are caused by at least one microorganism selected from the group consisting of *Phytophthora infestans, Rhizoctonia solani, Pythium ultimum, Botrytis cinerea, Alternaria solani, Colletotrichum cocodes, Alternaria brassicicola, Cladosporium cucumerinum, Monilinia fructicola, Venturia pyrina, Acidovorax avenae, Pseudomonas syringae, Xanthomonas campestris, Erwinia carotovora, Clavibacter michiganense, Plasmopara viticola, Sphaerotheca fuliginea, Uncinula necator,* and *Peronospora parasitica*.

19. The method of claim 13 wherein the *Bacillus subtilis* strain AQ713 is applied as a whole broth culture.

20. The method of claim 13, wherein the *Bacillus subtilis* strain AQ713 is applied as a supernatant.

21. The method of claim 19 wherein the *Bacillus subtilis* strain AQ713 is applied as wettable powders, granules, flowables or microencapsulations.

22. The method of claim 20, wherein the *Bacillus subtilis* strain AQ713 is applied as wettable powders, granules, flowables or microencapsulations.

23. The method of claims 13, 14 or 15 wherein the roots of plants or the soil around the roots are treated.

24. The method of claim 16 wherein the roots of plants or the soil around the roots are treated.

* * * * *

UNITED STATES PATENT AND TRADEMARK OFFICE
CERTIFICATE OF CORRECTION

PATENT : 6,060,051
DATED : May 9, 2000
INVENTOR(S) : Sherry Darlene Heins; Denise Carol Manker; Desmond Rito Jimenéz; Randy Jay McCoy; Pamela Gail Marrone; Jimmy Ensio Orjala It is certified that error appears in the above-identified patent and that said Letters Patent is hereby corrected as shown below:

Title page, Item 56,

In Other Publications, the citation reference to Bland et al. reading "Iturin-A" should read --Iturin-Arian--; the citation reference to Islam K.Z. reading "bacillus" and "Disease" should read --Bacillus-- and --Diseases--; the citation reference to Islam, et al. reading "Disease" should read --Diseases--; the citation reference to Kakinuma et al. reading "surfactiv" should read --surfactin--; the citation reference to Niskikiori et al. reading "Plipastatisn" and "A²" should read --Plipastatins-- and --A2--. Column 9, line 30 reading "Indole " should read --Indole - --. Column 13, line 19 that portion of the sequence reading "Tyr-Va" should read --Tyr-Val--. Column 17, Table 11 the portion reading "Metalaxy" should read --Metalaxyl--.

Signed and Sealed this

Twentieth Day of March, 2001

Attest:

NICHOLAS P. GODICI

*Attesting Officer*   *Acting Director of the United States Patent and Trademark Office*

SEQUENCE LISTING

```
<160> NUMBER OF SEQ ID NOS: 3

<210> SEQ ID NO 1
<211> LENGTH: 10
<212> TYPE: PRT
<213> ORGANISM: Bacillus subtilis
<220> FEATURE:
<221> NAME/KEY: VARIANT
<222> LOCATION: (1)...(1)
<223> OTHER INFORMATION: Gln or Glu
<220> FEATURE:
<221> NAME/KEY: VARIANT
<222> LOCATION: (2)...(2)
<223> OTHER INFORMATION: Orn
<220> FEATURE:
<221> NAME/KEY: VARIANT
<222> LOCATION: (5)...(5)
<223> OTHER INFORMATION: Gln or Glu
<220> FEATURE:
<221> NAME/KEY: VARIANT
<222> LOCATION: (6)...(6)
<223> OTHER INFORMATION: Ala or Val
<220> FEATURE:
<221> NAME/KEY: VARIANT
<222> LOCATION: (8)...(8)
<223> OTHER INFORMATION: Gln or Glu

<400> SEQUENCE: 1

Xaa Xaa Tyr Thr Xaa Xaa Pro Xaa Tyr Val
 1               5                   10

<210> SEQ ID NO 2
<211> LENGTH: 10
<212> TYPE: PRT
<213> ORGANISM: Bacillus subtilis
<220> FEATURE:
<221> NAME/KEY: VARIANT
<222> LOCATION: (2)...(2)
<223> OTHER INFORMATION: Orn

<400> SEQUENCE: 2
```

```
Glu Xaa Tyr Thr Glu Ala Pro Gln Tyr Val
1               5                   10

<210> SEQ ID NO 3
<211> LENGTH: 10
<212> TYPE: PRT
<213> ORGANISM: Bacillus subtilis
<220> FEATURE:
<221> NAME/KEY: VARIANT
<222> LOCATION: (2)...(2)
<223> OTHER INFORMATION: Orn

<400> SEQUENCE: 3

Glu Xaa Tyr Thr Glu Val Pro Gln Tyr Val
1               5                   10
```